United States Patent
Leech, Jr.

(10) Patent No.: US 11,723,885 B2
(45) Date of Patent: *Aug. 15, 2023

(54) METHODS AND COMPOSITIONS FOR INTERFERING WITH EXTRACTION OR CONVERSION OF A DRUG SUSCEPTIBLE TO ABUSE

(71) Applicant: Acura Pharmaceuticals, Inc., Palatine, IL (US)

(72) Inventor: Ronald L. Leech, Jr., Plymouth, IN (US)

(73) Assignee: Acura Pharmaceuticals, Inc., Palatine, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/521,581

(22) Filed: Nov. 8, 2021

(65) Prior Publication Data
US 2022/0062202 A1    Mar. 3, 2022

Related U.S. Application Data

(63) Continuation of application No. 16/803,474, filed on Feb. 27, 2020, now Pat. No. 11,197,837, which is a continuation of application No. 15/983,597, filed on May 18, 2018, now Pat. No. 10,610,497, which is a continuation of application No. 14/734,364, filed on Jun. 9, 2015, now Pat. No. 10,004,699.

(60) Provisional application No. 62/009,600, filed on Jun. 9, 2014.

(51) Int. Cl.

| *A61K 31/137* | (2006.01) |
|---|---|
| *A61K 9/20* | (2006.01) |
| *A61K 47/10* | (2017.01) |
| *A61K 47/12* | (2006.01) |
| *A61K 47/14* | (2017.01) |
| *A61K 47/32* | (2006.01) |
| *A61K 47/38* | (2006.01) |

(52) U.S. Cl.
CPC .......... *A61K 31/137* (2013.01); *A61K 9/2013* (2013.01); *A61K 9/2027* (2013.01); *A61K 9/2031* (2013.01); *A61K 9/2054* (2013.01); *A61K 9/2059* (2013.01); *A61K 47/10* (2013.01); *A61K 47/12* (2013.01); *A61K 47/14* (2013.01); *A61K 47/32* (2013.01); *A61K 47/38* (2013.01)

(58) Field of Classification Search
None
See application file for complete search history.

(56) References Cited

U.S. PATENT DOCUMENTS

| 4,800,083 | A | 1/1989 | Hom et al. |
|---|---|---|---|
| 8,901,113 | B2 | 12/2014 | Leech et al. |
| 9,101,636 | B2 | 8/2015 | Brzeczko et al. |
| 9,757,466 | B2 | 9/2017 | Leech et al. |
| 2006/0104909 | A1 | 5/2006 | Vaghefi et al. |
| 2006/0177380 | A1 | 8/2006 | Emigh et al. |
| 2009/0232887 | A1 | 9/2009 | Odidi et al. |
| 2011/0077238 | A1 | 3/2011 | Leech et al. |
| 2014/0112980 | A1 | 4/2014 | Vaghefi et al. |
| 2017/0143635 | A1 | 5/2017 | Leech et al. |

FOREIGN PATENT DOCUMENTS

| AU | 2014284333 A1 | 1/2016 |
|---|---|---|
| CN | 105338974 A | 2/2016 |
| WO | 2011066980 A2 | 6/2011 |
| WO | 2015003059 A1 | 1/2015 |

OTHER PUBLICATIONS

International Search Report for International Application PCT/US2015/034786 dated Aug. 27, 2015.
Written Opinion for International Application PCT/US2015/034786 dated Aug. 27, 2015.
Examination Report dated Sep. 28, 2017 issued in Australian Patent Application No. 2015274936.
Office Action dated Nov. 23, 2017 issued in Canadian Patent Application No. 2951563.
Extended European Search Report dated Oct. 18, 2017 issued in European Patent Application No. 15807096.1.
International Preliminary Report on Patentability dated Dec. 15, 2016 issued in International Patent Application No. PCT /US2015/034786.
State Intellectual Property Office, P.R. China, First Office Action, corresponding to Chinese Application No. 201580030318.7, dated May 26, 2018, 11 pages.
State Intellectual Property Office, P.R. China, Search Report, corresponding to Chinese Application No. 201580030318.7, dated May 26, 2018, 3 pages.
Examination Report dated Sep. 11, 2018 for Australian Patent Application No. 2015274936.
Office action dated Mar. 13, 2019 for Chinese Application No. 201580030318.7.

*Primary Examiner* — Samantha L Shterengarts
(74) *Attorney, Agent, or Firm* — DLA Piper LLP (US)

(57) ABSTRACT

Effective methods and compositions to deter abuse of pharmaceutical products (e.g., orally administered pharmaceutical products) including but not limited to immediate release, sustained or extended release and delayed release formulations for drugs subject to abuse.

25 Claims, No Drawings

METHODS AND COMPOSITIONS FOR INTERFERING WITH EXTRACTION OR CONVERSION OF A DRUG SUSCEPTIBLE TO ABUSE

CROSS-REFERENCE TO RELATED APPLICATIONS

This present application is a continuation of U.S. patent application Ser. No. 16/803,474, filed on Feb. 27, 2020, now allowed, which is a continuation of U.S. patent application Ser. No. 15/983,597, filed on May 18, 2018, now U.S. Pat. No. 10,610,497, which is a continuation of U.S. patent application Ser. No. 14/734,364, filed on Jun. 9, 2015, now U.S. Pat. No. 10,004,699, which claims the benefit of priority of U.S. Provisional Patent Application No. 62/009,600, filed on Jun. 9, 2014, each of which applications is incorporated by reference herein in its entirety.

BACKGROUND

Drug abusers and/or addicts typically may take a solid dosage form intended for oral administration containing one or more active drugs and crush, shear, grind, chew, dissolve and/or heat, extract or otherwise tamper with or damage the dosage form so that a significant portion or even the entire amount of the active drug becomes available for administration.

An abuser may convert a precursor compound found in a dosage form by illicit chemical processes. Examples of such methods include the Nazi Method, the Red Phosphorus Method, and the Shake and Bake Method.

The Shake and Bake Method is a method in which methamphetamine may be synthesized in a single container, also known as a "one-pot" system. Readily accessible non-polar solvents such as camp stove fuel (e.g. COLEMAN® Fuel) are often used in the Shake and Bake method.

There is a growing need for novel and effective methods and compositions to deter abuse of pharmaceutical products (e.g., orally administered pharmaceutical products) including but not limited to immediate release, sustained or extended release and delayed release formulations for drugs subject to abuse.

SUMMARY OF THE INVENTION

In certain embodiments therapeutic composition includes a pharmacologically effective amount of a drug susceptible to direct or indirect abuse, a triglyceride, hydroxypropylcellulose, polyethylene oxide, and a disintegrant selected from the group consisting of crospovidone, sodium starch glycolate and croscarmellose sodium. In some embodiments the drug susceptible to direct or indirect abuse is pseudoephedrine. In some embodiments, the therapeutic composition is an immediate release formulation.

In some embodiments, the drug susceptible to abuse comprises a water soluble drug or salt thereof. In some embodiments the drug susceptible to abuse comprises a precursor compound (e.g. pseudoephedrine) that can be chemically converted to a different drug (e.g. methamphetamine) that can then be directly abused. In some embodiments the pharmacologically effective amount of a drug susceptible to direct or indirect abuse is a pharmacologically effective amount of pseudoephedrine or a salt thereof.

In some embodiments, the drug susceptible to abuse comprises one or more of alfentanil, amphetamines, buprenorphine, butorphanol, carfentanil, codeine, dezocine, diacetylmorphine, dihydrocodeine, dihydromorphine, diphenoxylate, diprenorphine, etorphine, fentanyl, hydrocodone, hydromorphone, β-hydroxy-3-methylfentanyl, levo-α-acetylmethadol, levorphanol, lofentanil, meperidine, methadone, methylphenidate, morphine, nalbuphine, nalmefene, o-methylnaltrexone, naloxone, naltrexone, oxycodone, oxymorphone, pentazocine, pethidine, propoxyphene, remifentanil, sufentanil, tilidine, tramadol, and salts thereof.

In some embodiments, the hydroxypropylcellulose has a viscosity of about 1,500 mPa to about 3,000 mPa at a concentration of 1% in water. In some embodiments, the hydroxypropylcellulose has a molecular weight of about 1,150,000.

In some embodiments, the polyethylene oxide is present in an amount of about 3 wt % to about 7 wt %. In some embodiments, the polyethylene oxide is present in an amount of about 5 to about 10 wt %. In some embodiments, the crospovidone is present in an amount of about 15 wt % to about 25 wt %; or about 18 wt % to about 22 wt %.

In some embodiments, the triglyceride has a melting point of about 50° C. to about 80° C. In some embodiments the triglyceride is tristearin.

In certain embodiments, a composition suitable for reducing the chemical conversion of precursor compounds included in the composition to a drug susceptible to abuse includes a precursor compound that can be used in a chemical synthesis of a drug that is susceptible to abuse; a triglyceride, hydroxypropylcellulose; polyethylene oxide; and a disintegrant selected from the group consisting of crospovidone, sodium starch glycolate and croscarmellose sodium. In some embodiments, the precursor compound includes pseudoephedrine or salts thereof, (e.g. pseudoephedrine HCl). In some embodiments, the composition is an immediate release composition. In some embodiments the unit does form is a direct compressed unit dose form.

In certain embodiments a method of making a composition suitable for reducing the chemical conversion of precursor compound included in the composition to a drug susceptible to abuse includes providing ingredients comprising: a precursor compound that can be used in a chemical synthesis of a drug that is susceptible to abuse; a triglyceride, hydroxypropylcellulose; polyethylene oxide, and a disintegrant selected from the group consisting of crospovidone, sodium starch glycolate, and croscarmellose sodium; and directly compressing the ingredients into a unit dose form.

DETAILED DESCRIPTION OF THE INVENTION

The present invention restricts, reduces or diminishes the crystallization and/or extraction of a drug that has been converted by illicit means from a precursor drug. In some embodiments the present invention provides a pharmaceutical composition that includes a therapeutically active pharmaceutical with one or more triglycerides that are soluble in a non-polar solvent.

Without being bound by a particular mode of action, in some embodiments, therapeutic compositions of the present invention can interfere with the crystallization of a drug susceptible to abuse by forming a complex in solution with the converted drug. The triglyceride present in compositions of some embodiments of the present invention is soluble in non-polar organic solvents. Examples of such drugs susceptible to abuse are methamphetamine or methionine, which have been converted from a precursor drug such as pseudoephedrine, obtained from a pseudoephedrine dosage form. Examples of such non-polar solvents include, but are not limited to, cyclohexane, nonane, octane, heptane, pentane, and mixtures thereof, including, but not limited to COLEMAN® Fuel (also referred to as naptha or white gas).

A. Constituents of an Abuse Deterrent Formulation

1. Drugs Suitable for Use with the Present Invention

In some embodiments, the drug for use in the present invention can include precursor compounds which can be converted to other abusable drugs and include, but are not limited to, sympathomimetic amines, amphetamine-like compounds, amphetamine and methamphetamine precursors including ephedrine, norpseudoephedrine, pseudoephedrine, pseudoephedrine HCl, pseudoephedrine sulfate, phenylpropanolamine, methyl phenidate, and salts, derivatives, analogs, homologues, polymorphs thereof, and mixtures of any of the foregoing. In some embodiments, the drug for use in the present invention can include pseudoephedrine HCl.

Any drug, therapeutically acceptable drug salt, drug derivative, drug analog, drug homologue, or polymorph can be used in the present invention. In one embodiment, the drug is an orally administered drug. In certain embodiments, drugs susceptible to abuse are used. Drugs commonly susceptible to abuse include psychoactive drugs and analgesics, including but not limited to opioids, opiates, stimulants, tranquilizers, narcotics and drugs that can cause psychological and/or physical dependence. In some embodiments, the present invention can include any of the resolved isomers of the drugs described herein, and/or salts thereof.

In some embodiments, a drug for use in the present invention which can be susceptible to abuse can be one or more of the following: alfentanil, amphetamines, buprenorphine, butorphanol, carfentanil, codeine, dezocine, diacetylmorphine, dihydrocodeine, dihydromorphine, diphenoxylate, diprenorphine, etorphine, fentanyl, hydrocodone, hydromorphone, β-hydroxy-3-methylfentanyl, levo-α-acetylmethadol, levorphanol, lofentanil, meperidine, methadone, methylphenidate, morphine, nalbuphine, nalmefene, o-methylnaltrexone, naloxone, naltrexone, oxycodone, oxymorphone, pentazocine, pethidine, propoxyphene, remifentanil, sufentanil, tilidine and tramodol, salts, derivatives, analogs, homologues, polymorphs thereof, and mixtures of any of the foregoing.

In some embodiments, a drug for use with the present invention which can be susceptible to abuse includes one or more of the following: N-{1-[2-(4-ethyl-5-oxo-2-tetrazolin-1-yl)-ethyl]-4-methoxymethyl-4-piperi-dyl}propionanilide (alfentanil), 5,5-diallyl barbituric acid (allobarbital), allylprodine, alpha-prodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methyl phenethylamine (amphetamine), 2-(α-methylphenethyl-amino)-2-phenyl acetonitrile (amphetaminil), 5-ethyl-5-isopentyl barbituric acid (amobarbital), anileridine, apocodeine, 5,5-diethyl barbituric acid (barbital), benzylmorphine, bezitramide, 7-bromo-5-(2-pyridyl)-1H-1,4-benzodiazepin-2(3H)-one (bromazepam), 2-bromo-4-(2-chlorophenyl)-9-methyl-6H-thieno[3,2-f][1,2,4]-triazolo[4,3-a][1,4]diazepine (brotizolam), 17-cyclopropylmethyl-4,5 α-epoxy-7α[(S)-1-hydroxy-1,2,2-trimet-hylpropyl]-6-methoxy-6,14-endo-ethanomorphinan-3-ol (buprenorphine), 5-butyl-5-ethyl barbituric acid (butobarbital), butorphanol, (7-chloro-1,3-dihydro-1-methyl-2-oxo-5-phenyl-2H-1,4-benzodiazepin-3-yl)-dimethyl carbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine-4 oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]-diazepin-2(3H)-one (clotiazepam), 10-chloro-11b-(2-chlorophenyl)-2,3,7,11b-tetrahydrooxazolo[3,2-d][1,4]benzodiazepin-6(5H)-one (cloxazolam), (−)-methyl-[3β-benzoyloxy-2β(1αH,5αH)-tropane carboxylate (cocaine), 4,5α-epoxy-3-methoxy-17-methyl-7-morphinen-6α-ol (codeine), 5-(1-cyclohexenyl)-5-ethyl barbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethyl-amino-2-methyl-1-phenylpropyl)propionate (dextropropoxyphene), dezocine, diampromide, diamorphone, 7-chloro-1-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6a-morphinandiol (dihydromorphine), dimenoxadol, dimephetamol [sic-Tr.Ed.], dimethyl thiambutene, dioxaphetyl butyrate, dipipanone, (6aR,10aR)-6,6,9-trim-ethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethyl methyl thiambutene, ethyl-[7-chloro-5-(2-fluorophenyl)-2,3-dihydro-2-oxo-1H-1,4-benzodiazepin- -3-carboxylate] (ethyl loflazepate), 4,5α-epoxy-3-ethoxy-17-methyl-7-morphinen-6α-ol (ethylmorphine), etonitrazene, 4,5α-epoxy-7α-(1-hydroxy-1-methylbutyl)-6-methoxy-17-methyl-6-,14-endo-etheno-morphinan-3-ol (etorphine), N-ethyl-3-phenyl-8,9,10-trinorbornan-2-ylamine (fencamfamine), 7-[2-(α-methylphenethylamino)-ethyl] theophylline (fenethylline), 3-(α-methylphenethylamino) propionitrile (fenproporex), N-(1-phenethyl-4-piperidyl) propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2-(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolo[3,2-d][1,4-]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinan, 11-chloro-8,12b-dihydro-2,8-dimethyl-12b-phenyl-4H-[1,3]oxazino[3,2-d][1,-4]benzodiazepin-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenyl-heptan-3-yl acetate (levacetylmethadol (LAAM)), (−)-6-dimethylamino-4,4-diphenyl-3-heptanone (levomethadone), (−)-17-methyl-3-morphinanol (levorphanol), levophenacylmorphan, lofentanil, 6-(2-chlorophenyl)-2-(4-methyl-1-piperazinylmethylene)-8-nitro-2H-imidazo-[1,2a][1,4]benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)- -one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyl trimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl-[2-phenyl-2-(2-piperidyl)acetate] (methyl phenidate), 5-ethyl-1-methyl-5-phenyl barbituric acid (methyl phenobarbital), 3,3-diethyl-5-methyl-2,4-piperidinedione (methyprylon), metopon, 8-chloro-6-(2-fluorophenyl)-1-methyl-4H-imidazo[1,5-a][1,4]benzodiazepine (midazolam), 2-(benzhydrylsulfinyl)acetamide (modafinil), 4,5α-epoxy-17-methyl-7-morphinene-3,6α-diol (morphine), myrophine, (±)-trans-3-(1,1-dimethylheptyl)-7,8,10,10a-tetrahydro-1-hydroxy- -6, 6-dimethyl-6H-dibenzo[b,d]pyran-9(6αH)-one (nabilone), nalbuphen, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2-(3H)-one (nordazepam), norlevorphanol, 6-dimethylamino-4,4-diphenyl-3-hexanone (normethadone), normorphine, norpipanone, the coagulated juice of the plants belonging to the species *Papaver somniferum* (opium), 7-chloro-3-hydroxy-5-phenyl-1H-1,4-benzodiazepin-2-(3H)-one (oxazepam), (cis-trans)-10-chloro-2,3,7, 11b-tetrahydro-2-methyl-11b-phenyloxazolo[3,2- -d][1,4] benzodiazepin-6-(5H)-one (oxazolam), 4,5α-epoxy-14-hydroxy-3-methoxy-17-methyl-6-morphinanone (oxycodone), oxymorphone, plants and plant parts of the plants belonging to the species *Papaver somniferum* (including the subspecies *setigerum*) (*Papaver somniferum*), papaveretum, 2-imino-5-phenyl-4-oxazolidinone (pemoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)barbituric acid (pentobarbital), ethyl-(1-methyl-4-phenyl-4-piperidine-carboxylate) (pethidine), phenadoxone, phenomorphan, phenazocine, phenoperidine, piminodine, pholcodeine, 3-methyl-2-phenyl morpholine (phenmetrazine), 5-ethyl-5-phenyl barbituric acid (phenobarbital), α,α-dimethyl phenethylamine (phentermine), 7-chloro-5-phenyl-1-(2-propinyl)-1H-1,4-benzodiazepin-2 (3H)-one (pinazepam), α-(2-piperidyl)benzhydryl alcohol (pipradol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl)propionamide, methyl-{3-[4-methoxycarbonyl-4-(N-phenylpropaneamido)piperidino]propanoat-e}(remifentanil), 5-sec.-butyl-5-ethyl barbituric acid (secbutabarbital), 5-allyl-5-(1-methylbutyl)barbituric acid (secobarbital), N-{4-methoxymethyl-1-[2-(2-thienyl)ethyl]-4-piperidyl}propionanilide (sufentanil), 7-chloro-2-hydroxymethyl-5-phenyl-1H-1,4-benzodiazepin-2-(3H)-one (temazepam), 7-chloro-5-(1-cyclohexenyl)-1-methyl-1H-1,4-benzodiazepin-2(3H)-one (tetrazepam), ethyl-(2-dimethylamino-1-phenyl-3-cyclohexane-1-carboxylate) (tilidine-(cis and trans)), tramadol, 8-chloro-6-(2-chlorophenyl)-1-methyl-4H-[1,2,4]triazolo[4,3-a][1,4]benzod-iazepine (triazolam), 5-(1-methylbutyl)-5-vinyl barbituric acid (vinylbital), (1R*,2R*)-3-(3-dimethylamino-1-ethyl-2-methyl-propyl)phenol, (1R,2R,4S)-2-[dimethylamino) methyl-4-(p-fluorobenzyloxy)-1-(m-methoxyphenyl)cyclohexanol, each optionally in the form of corresponding stereoisomeric compounds as well as corresponding derivatives, especially esters or ethers, and all being physiologically compatible compounds, especially salts and solvates.

In some embodiments a drug may be present in a therapeutic composition in a pharmacologically effective amount. In some embodiments, a drug may be present in a therapeutic composition in an amount of about 1 wt % to about 25 wt %; about 1 wt % to about 22 wt %; about 1 wt % to about 20 wt %; about 1 wt % to about 18 wt %; about 1 wt % to about 16 wt %; about 1 wt % to about 14 wt %; about 1 wt % to about 12 wt %; about 2 wt % to about 10 wt %; about 2 wt % to about 8 wt %; about 3 wt % to about 8 wt %; about 4 wt % to about 7 wt %; about 5 wt % to about 7 wt %, or about 6 wt % to about 7 wt %. In some embodiments, a drug may be present in a therapeutic composition in an amount of about 1 wt %; about 1.5 wt %; about 2 wt %; about 2.5 wt %; about 3 wt %; about 3.5 wt %; about 4 wt %; about 4.5 wt %; about 5 wt %; about 5.5 wt %; about 6 wt %; about 6.5 wt %; about 7 wt %; about 7.5 wt %; about 8 wt %; about 8.5 wt %; about 9 wt %; about 9.5 wt %; about 10 wt %; about 10.5 wt %; about 11 wt %; about 11.5 wt %; about 12 wt %; about 12.5 wt %; about 13 wt %; about 13.5 wt %; about 14 wt %; about 14.5 wt %; about 15 wt %; about 15.5 wt %; about 16 wt %; about 16.5 wt %; about 17 wt %; about 17.5 wt %; about 18 wt %; about 18.5 wt %; about 19 wt %; about 19.5 wt %; about 20 wt %; about 21 wt %; about 22 wt %; about 23 wt %; about 24 wt %; or about 25 wt %. In some embodiments, a drug may be present in a therapeutic composition in an amount of about 6.12 wt %.

In some embodiments, a drug is present in a therapeutic composition in an amount of about 1 mg, about 2 mg, about 3 mg, about 4 mg, about 5 mg, about 6 mg, about 7 mg, about 8 mg, about 9 mg, about 10 mg, about 11 mg, about 12, mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg; about 225 mg, about 240 mg, or about 250 mg.

In some embodiments, a pharmaceutical composition of the present invention includes one or more opioids such as hydrocodone, morphine and oxycodone and/or salts thereof, as the therapeutically active ingredient. Typically when processed into a suitable dosage form, the drug can be present in such dosage forms in an amount normally prescribed, typically about 0.5 to about 25 percent on a dry weight basis, based on the total weight of the formulation.

In some embodiments, a pharmaceutical composition of the present invention includes one or more analgesics that are not typically susceptible to abuse, such as acetominophen (also referred to as paracetamol, APAP, or N-acetyl-p-aminophenol), salts thereof, or formulations thereof (e.g. COMPAP™ L), in addition to a drug which is susceptible to abuse, described above. Typically when processed into a suitable dosage form, the analgesic can be present in such dosage forms in an amount normally prescribed, typically about 0.5 to about 50 percent on a dry weight basis, based on the total weight of the formulation. In some embodiments the analgesic can be present in an amount of about 10 percent to about 40 percent, about 15 percent to about 35 percent, or about 20 percent to about 25 percent. In some embodiments the analgesic can be present in an amount of about 5 percent, about 10 percent, about 15 percent, about 20 percent, about 25 percent, about 30 percent, about 35 percent, about 40 percent, about 45 percent, or about 50 percent.

With respect to analgesics in unit dose form, such an amount can be typically from about 5, 25, 50, 75, 100, 125, 150, 175 or 200 mg. More typically, the analgesic that is not typically susceptible to abuse can be present in an amount from 5 to 500 mg or even 5 to 200 mg. In some embodiments, a dosage form contains an appropriate amount of analgesic that is not typically susceptible to abuse to provide a therapeutic effect.

In some embodiments, the present invention includes one or more constituents which may or may not have pharmacological activity and that are not typically susceptible to abuse in addition to a drug that is susceptible to abuse, described above. In certain embodiments, the one or more constituents that are not typically susceptible to abuse can have an abuse deterrent effect (as described in more detail below) when administered in combination with a drug which is susceptible to abuse. In one embodiment of a dosage form of the present invention which includes a drug that is susceptible to abuse, the one or more additional drugs which can induce an abuse deterrent effect can be included in the dosage form in a sub-therapeutic or sub-clinical amount.

As used herein, "sub-therapeutic" or "sub-clinical" refer to an amount of a referenced substance that if consumed or otherwise administered, is insufficient to induce an abuse deterrent effect (e.g., nausea) in an average subject or is insufficient to meet or exceed the threshold dose necessary for inducing an abuse deterrent effect.

Accordingly, when an embodiment of a dosage form of the present invention is administered in accordance with a health care provider prescribed dosage and/or manner, the one or more additional drugs which can induce an abuse deterrent effect will not be administered in an amount sufficient to induce an abuse deterrent effect. However, when a certain embodiment of the present invention is administered in a dose and/or manner that is different from a health care provider prescribed dose, (i.e., the drug is abused or the dosage form is tampered with) the content of a formulation which can cause an abuse deterrent effect according to the present invention will be sufficient to induce an abuse deterrent effect. Suitable examples of drugs which can be administered in sub-therapeutic amounts in the present invention include niacin, atropine sulfate, homatropine methylbromide, sildenafil citrate, nifedipine, zinc sulfate, dioctyl sodium sulfosuccinate and capsaicin.

2. Lipids, Triglycerides, and Other Constituents Soluble in a Non-Polar Solvent

As described above, the present invention can include one or more triglycerides, and in particular triglycerides that are soluble in a non-polar solvent. In other embodiments, the present invention can include one or more lipids, such as fatty acids or esters. In still other embodiments, the present invention can include one or more other constituents that are soluble in a non-polar solvent. In some embodiments the present invention can include a combination of one or more triglycerides, lipids, and other constituents that are soluble in a non-polar solvent.

Suitable triglycerides include triglycerides that are soluble in non-polar solvents, and upon dissolution in the non-polar solvent together with one or more drugs, remain in the non-polar solvent and interfere with the conversion of a precursor compound to a drug, and/or interfere with crystallization and extraction of a drug (e.g. the same drug as originally in the dosage form) or a drug converted from the one or more precursor drugs (e.g. methamphetamine), significantly reducing or eliminating the amount of drug that can be recovered from an illicit recovery method.

In some embodiments, the triglyceride can prevent conversion of a precursor compound (e.g. pseudoephedrine) to a drug susceptible to abuse (e.g. methamphetamine). Without being bound by a particular theory, lithium used in the one-pot method reacts preferentially with the triglyceride, necessitating additional lithium to convert the precursor compound to the drug. The inclusion of triglyceride, therefore, results in either incomplete conversion of precursor compound, or a higher cost (i.e. the cost of additional lithium) to complete the illicit conversion.

Without wishing to be bound by a particular theory, when the drug is a precursor compound (e.g. pseudoephedrine), the triglyceride can interfere with the crystallization of the converted drug by forming a complex with the converted drug in solution and can interfere with the extraction of the converted drug both by forming a complex with the converted drug and by prolonging the process of filtering the converted drug from the non-polar solvent. Unexpectedly, the inclusion of a triglyceride in compositions of the invention results in an undesirably low yield of converted drug that can be isolated.

In some embodiments, a suitable triglyceride is solid at room temperature (about 20° C.).

Suitable triglycerides can include compounds such as triacetin, butyrin, tricaprylin, triheptanoin, trimyristin, trilinolein, triolein, tristearin (also referred to as stearin or glycerol stearate), tripalmitin, hydrogenated palm kernel oil, and hydrogenated palm oil.

Suitable lipids include, but are not limited to, fatty acids and mixtures of fatty acids (e.g. sesame oil).

Other constituents that are soluble in a non-polar solvent include, but are not limited to, monoglycerides (e.g. MYVACET® available from Kerry, Inc.), and tocopherols (e.g. vitamin E).

An example of suitable, commercially available triglyceride includes DYNASAN 118® Tristearin from CREMER OLEO GmbH & Co. KG. An example of another suitable, commercially available triglyceride includes SOFTISAN 154® hydrogenated palm kernel oil from CREMER OLEO GmbH & Co. KG.

In some embodiments the melting point of the triglyceride is at least about 40° C., 45° C., 50° C., 55° C., 60° C., 65° C., 60° C., 75° C., and 80° C. In some embodiments the melting point of the triglyceride is in the range of about 40° C. to about 50° C., about 45° C. to about 55° C., about 50° C. to about 60° C., about 55° C. to about 65° C., about 60° C. to about 70° C., about 65° C. to about 75° C., and preferably about 70° C. to about 80° C. In some embodiments it has been advantageously found that by including a triglyceride with a higher melting point, a formulation of the invention can withstand heat generated during a process of manufacturing a dosage form, such as heat from a high speed press during direct compression of a tablet formulation. Thus, standard manufacturing techniques can be used with certain formulations of the present invention.

In some embodiments, a therapeutic composition includes a triglyceride in an amount of about 1 wt % to about 50 wt %; about 1 wt % to about 45 wt %; about 1 wt % to about 40 wt %; about 1 wt % to about 35 wt %; about 1 wt % to about 30 wt %; about 1 wt % to about 25 wt %; about 1 wt % to about 20 wt %; about 5 wt % to about 15 wt %; about 6 wt % to about 13.5 wt %; about 6.5 wt %; to about 13.5 wt %; about 7 wt % to about 13 wt %; about 7.5 wt % to about 12.5 wt %; about 8 wt % about 12 wt %; about 8.5 wt % to about 11.5 wt %; about 9 wt % to about 11 wt %; about 9.5 wt % to about 10.5 wt %; or about 10 wt % to about 10.5 wt %.

In some embodiments, a therapeutic composition includes a triglyceride in an amount of at least about 1 wt %; at least about 3 wt %; at least about 5 wt %; at least about 8 wt %; at least about 10 wt %; at least about 12 wt %; at least about 15 wt %, at least about 18 wt %; or at least about 20 wt %.

In some embodiments, a therapeutic composition includes a triglyceride in an amount of about 1 wt %; about 1.5 wt % about 2 wt %; about 2.5 wt %; about 3 wt %; about 3.5 wt %; about 4 wt %; about 4.5 wt %; about 5.0 wt %; about 5.5 wt %; about 6 wt %; about 6.5 wt %; about 7 wt %; about 7.5 wt %; about 8 wt %; about 8.5 wt %; about 9 wt %; about 9.5 wt %; about 9.6 wt %; about 9.7 wt %; about 9.8 wt %; about 9.9 wt %; about 10.0 wt %; about 10.1 wt %; about 10.2 wt %; about 10.3 wt %; about 10.4 wt %; about 10.5 wt %; about 10.6 wt %; about 10.7 wt %; about 10.8 wt %; about 10.9 wt %; about 11 wt %; 11.5 wt % to about 12 wt %; about 12.5 wt %; about 13 wt %; about 13.5 wt %; about 14 wt %; about 14.5 wt %; about 15.0 wt %; about 15.5 wt %; about 16 wt %; about 16.5 wt %; about 17 wt %; about 17.5 wt %; about 18 wt %; about 18.5 wt %; about 19 wt %; about 19.5 wt %; or about 20 wt %.

In some embodiments, a therapeutic composition includes a triglyceride in an amount of about 20 mg to about 120 mg; about 20 mg to about 115 mg; about 20 mg to about 110 mg; about 20 mg to about 105 mg; about 20 mg to about 100 mg; about 20 mg to about 95 mg; about 20 mg to about 90 mg; about 20 mg to about 85 mg; about 20 mg to about 80 mg; about 25 mg to about 75 mg; about 30 mg to about 70 mg; about 35 mg to about 65 mg; about 40 mg to about 60 mg; or about 45 mg to about 55 mg. In some embodiments, a therapeutic composition includes polyethylene oxide in an amount of about 20 mg; about 25 mg; about 30 mg; about 35 mg; about 40 mg; about 45 mg; about 46 mg; about 47 mg; about 48 mg; about 49 mg; about 50 mg; about 51 mg; about 52 mg; about 53 mg; about 54 mg; about 55 mg; about 60 mg; about 65 mg; about 70 mg; about 75 mg; about 80 mg; about 85 mg; about 90 mg; about 95 mg; about 100 mg; about 105 mg; about 110 mg; about 115 mg; or about 120 mg.

3. Viscosity Increasing/Gel Forming Agents

As described above, the present invention can include one or more viscosity increasing or gel forming agents (hereafter referred to as gel forming agents) which form a gel upon contact with a solvent.

Suitable gel forming agents include compounds that, upon contact with a solvent, absorb the solvent and swell, thereby forming a viscous or semi-viscous substance that significantly reduces and/or minimizes the amount of free solvent which can contain an amount of solubilized drug, and which can be drawn into a syringe. The viscous or gelled material can also reduce the overall amount of drug extractable with the solvent by entrapping the drug in a gel matrix. In some embodiments, suitable gel forming agents include pharmaceutically acceptable polymers, including hydrophilic polymers, such as hydrogels.

As noted in U.S. Publication No. 2006/0177380 and other references, suitable polymers exhibit a high degree of viscosity upon contact with a suitable solvent. The high viscosity can enhance the formation of highly viscous gels when attempts are made by an abuser to crush and dissolve the contents of a dosage form in an aqueous vehicle and inject it intravenously.

More specifically, in certain embodiments the polymeric material in the present invention forms a viscous or gelled material upon tampering. In such embodiments, when an abuser crushes and dissolves the dosage form in a solvent, a viscous or semi-viscous gel is formed. The increase in the viscosity of the solution discourages the abuser from injecting the gel intravenously or intramuscularly by preventing the abuser from transferring sufficient amounts of the solution to a syringe to cause a desired "high" once injected. In some embodiments, the increase in viscosity of the solution discourages the use of legitimate, over the counter, and/or prescription drugs that are included in embodiments of the present invention in the illicit manufacture of other drugs. Specifically, the gel restricts the solubilization of the drug prior to the conversion of the drug to another drug, e.g., the illicit use of pseudoephedrine in the manufacture of methamphetamine or methcathinone, as described below.

In certain embodiments, suitable polymers include one or more pharmaceutically acceptable polymers selected from any pharmaceutical polymer that will undergo an increase in viscosity upon contact with a solvent, e.g., as described in U.S. Pat. No. 4,070,494, the entire content of which is hereby incorporated by reference. Suitable polymers can include alginic acid, polyacrylic acid, karaya gum, tragacanth, polyethylene oxide, polyvinyl alcohol, hydroxypropylcellulose, and methyl cellulose including sodium carboxy methyl cellulose, hydroxyethyl methyl cellulose hydroxypropyl methyl cellulose and carbomers. In some embodiments, a therapeutic composition includes a combination of polyethylene oxide, and hydroxypropylcellulose. Other embodiments further include ethylcellulose.

Polyethylene Oxide

In some embodiments, the therapeutic composition includes polyethylene oxide. In certain embodiments, the polyethylene oxide can have an average molecular weight ranging from at least about 300,000 to about 5,000,000; about 600,000 to about 5,000,000; about 800,000 to about 5,000,000; about 1,000,000 to about 5,000,000; about 3,000,000 to about 5,000,000; about 3,000,000 to about 8,000,000; and preferably at least about 5,000,000. In one embodiment, the polyethylene oxide includes a high molecular weight polyethylene oxide.

In one embodiment, the average particle size of the polyethylene oxide ranges from about 840 to about 2,000 microns. In another embodiment, the density of the polyethylene oxide can range from about 1.15 to about 1.26 g/ml. In another embodiment, the viscosity can range from about 8,800 to about 17,600 cps.

A suitable polyethylene oxide used in a directly compressible formulation of the present invention may be a homopolymer having repeating oxyethylene groups, i.e., $-(-O-CH_2-CH_2-)_n-$, where n can range from about 2,000 to about 180,000. In some embodiments, the polyethylene oxide is a commercially available and pharmaceutically acceptable homopolymer having moisture content of no greater than about 1% by weight. Examples of suitable, commercially available polyethylene oxide polymers include Polyox®, WSRN-1105 and/or WSR-coagulant, available from Dow chemicals. In another embodiment, the polymer can be a copolymer, such as a block copolymer of PEO and PPO. In some embodiments, the polyethylene oxide powdered polymers can contribute to a consistent particle size in a directly compressible formulation and eliminate the problems of lack of content uniformity and possible segregation.

In some embodiments, a therapeutic composition includes polyethylene oxide in an amount of about 1 wt % to about 10 wt %; about 1.5 wt %; to about 9 wt %; about 1.5 wt %; to about 8.5 wt %; about 2 wt % to about 8 wt %; about 2.5 wt % to about 7.5 wt %; about 3 wt % to about 7 wt %; about 3.5 wt % to about 6.5 wt %; about 4 wt % to about 6 wt %; about 4.5 wt % to about 5.5 wt %; or about 5 wt % to about 5.5 wt %.

In some embodiments, a therapeutic composition includes polyethylene oxide in an amount of about 1 wt %; about 1.5 wt % about 2 wt %; about 2.5 wt %; about 3 wt %; about 3.5 wt %; about 4 wt %; about 4.5 wt %; about 4.6 wt %; about 4.7 wt %; about 4.8 wt %; about 4.9 wt %; about 5.0 wt %; about 5.1 wt %; about 5.2 wt %; about 5.3 wt %; about 5.4 wt %; about 5.5 wt %; about 5.6 wt %; about 5.7 wt %; about 5.8 wt %; about 5.9 wt %; about 6 wt %; about 6.5 wt %; about 7 wt %; about 7.5 wt %; 8 wt %; about 8.5 wt %; about 9 wt %; about 9.5 wt %; or about 10 wt %.

In some embodiments, a therapeutic composition includes polyethylene oxide in an amount of about 5 mg to about 55 mg; about 5 mg to about 50 mg; about 5 mg to about 45 mg; about 10 mg to about 40 mg; about 15 mg to about 35 mg; or about 20 mg to about 30 mg. In some embodiments, a therapeutic composition includes polyethylene oxide in an amount of about 5 mg; about 10 mg; about 15 mg; about 30 mg; about 40 mg; about 45 mg; about 50 mg; or about 55 mg.

Constituents which Gels in Polar and Non-Polar Solvents

In some embodiments, the therapeutic composition includes a constituent which gels in an organic solvent. In some embodiments, the therapeutic composition includes a constituent which gels in a non-polar solvent. In some embodiments, the therapeutic composition includes a constituent which gels in a polar solvent. In some embodiments, the therapeutic composition includes hydroxypropylcellulose. While hydroxyproylcellulose can form a gel when in contact with water, it can also form a gel when in contact with organic solvents, particularly certain dry organic solvents, e.g., ethyl alcohol.

In some embodiments, suitable hydroxypropylcellulose has a molecular weight of about 600,000 to about 1,300,000; about 1,000,000 to about 1,300,000; about 1,100,000 to about 1,200,000; or about 1,150,000.

As noted above, high viscosity can enhance the formation of highly viscous gels when attempts are made by an abuser to crush and dissolve the contents of a dosage form in an aqueous vehicle and inject it intravenously. However, in certain embodiments, it has been found that in the context of abuse deterrence selection of a lower viscosity hydroxypropylcellulose is suitable.

Accordingly, in certain embodiments, suitable hydroxypropylcellulose has a viscosity of about 1,500 mPa to about 6,500 mPa; about 2,000 mPa to about 6,500 mPa; about 2,500 mPa to about 6,500 mPa; about 3,000 mPa to about 6,500 mPa; about 3,500 to about 6,500 mPa; about 4,000 mPa to about 6,500 mPa; about 4,500 mPa to about 6,000 mPa; about 5,000 mPa to about 5,500 mPa; about 1,500 mPa to about 3,000 mPa; about 2,000 mPa to about 2,500 mPa; about 1,500 mPa to about 3,500 mPa; about 1,500 mPa to about 4,000 mPa; about 1,500 mPa to about 4,500 mPa; about 1,500 mPa to about 5,000 mPa; about 1,500 mPa to about 5,500 mPa; or about 1,500 to about 6,000 mPa. In some embodiments, suitable hydroxypropylcellulose has a viscosity of about 1,500 mPa; about 1,750 mPa, about 2,000 mPa; about 2,250 mPa; about 2,500 mPa; about 2,750 mPa; about 3,000 mPa; about 3,500 mPa; about 4,000 mPa; about 4,500 mPa; about 5,000 mPa; about 5,500 mPa; about 6,000 mPa; or about 6,500 mPa.

In some embodiments, suitable hydroxypropylcellulose has a $D^{50}$ particle size of about 400 μm to about 1,000 μm; about 800 μm to about 1,000 μm; about 850 μm to about 950 μm; about 900 μm to about 950 μm; about 900 μm to about 930 μm; about 910 μm to about 920 μm; about 400 μm to about 650 μm; about 450 μm to about 600 μm; about 500 μm to about 550 μm; or about 510 μm to about 530 μm. In some embodiments, suitable hydroxypropylcellulose has a Du particle size of about 400 μm; about 425 μm; about 450 μm; about 475 μm; about 500 μm; about 501 μm; about 502 μm; about 503 μm; about 504 μm; about 505 μm; about 506 μm; about 507 μm; about 508 μm; about 509 μm; about 510 μm; about 511 μm; about 512 μm; about 513 μm; about 514 μm; about 515 μm; about 516 μm; about 517 μm; about 518 μm; about 519 μm; about 520 μm; about 521 μm; about 522 μm; about 523 μm; about 524 μm; about 525 μm; about 526 μm; about 527 μm; about 528 μm; about 529 μm; about 530 μm; about 531 μm; about 532 μm; about 533 μm; about 534 μm; about 535 μm; about 536 μm; about 537 μm; about 538 μm; about 539 μm; about 540 μm; about 550 μm; about 575 μm; about 600 μm; about 625 μm; about 650 μm; about 675 μm; about 700 μm; about 725 μm; about 750 μm; about 775 μm; about 800 μm; about 825 μm; about 850 μm; about 875 μm; about 900 μm; about 925 μm; about 950 μm; about 975 μm; or about 1000 μm.

In certain embodiments, suitable hydroxypropylcellulose has a tap density of about 0.493 g/cm$^3$ to about 0.552 g/cm$^3$; about 0.498 g/cm$^3$ to about 0.547 g/cm$^3$; about 0.503 g/cm$^3$ to about 0.542 g/cm$^3$; about 0.508 g/cm$^3$ to about 0.537 g/cm$^3$; about 0.493 g/cm$^3$ to about 0.523 g/cm$^3$; about 0.498 g/cm$^3$ to about 0.518 g/cm$^3$; about 0.503 g/cm$^3$ to about 0.513 g/cm$^3$; or about 0.506 g/cm$^3$ to about 0.51 g/cm$^3$. In some embodiments, suitable hydroxypropylcellulose has a tap density of about 0.493 g/cm$^3$; about 0.498 g/cm$^3$; about 0.503 g/cm$^3$; about 0.504 g/cm$^3$; about 0.505 g/cm$^3$; about 0.506 g/cm$^3$; about 0.507 g/cm$^3$; about 0.508 g/cm$^3$; about 0.509 g/cm$^3$; about 0.510 g/cm$^3$; about 0.511 g/cm$^3$; about 0.512 g/cm$^3$; about 0.517 g/cm$^3$; about 0.522 g/cm$^3$; about 0.527 g/cm$^3$; about 0.532 g/cm$^3$; about 0.537 g/cm$^3$; about 0.542 g/cm$^3$; about 0.547 g/cm$^3$; about 552 g/cm$^3$.

An example of suitable, commercially available hydroxypropylcellulose includes Klucel® Hydroxypropylcellulose from Aqualon Hercules, Inc.

Hydroxypropylcellulose is known in industry (like polyethylene oxide) as a polymer that is used in drug product matrices for creating a sustained release profile. In sustained release forms, the typical concentrations range from about 15% to about 35% hydroxypropylcellulose. In certain embodiments, the present invention can include about 20% to about 40% hydroxypropylcellulose without compromising immediate release characteristics. Immediate release characteristics are understood to include the release of an active promptly after administration.

In some embodiments, a therapeutic composition includes hydroxypropylcellulose in an amount of about 5 wt % to about 35 wt %; about 10 wt % to about 20 wt %; about 15 wt % to about 25 wt %; about 18 wt % to about 22 wt %; or about 19 wt % to about 21 wt %, or about 20% to about 40%. In some embodiments, a therapeutic composition includes hydroxypropylcellulose in an amount of about 5 wt %; about 6 wt %; about 7 wt %; about 8 wt %; about 9 wt %; about 10 wt %; about 11 wt %; about 12 wt %; about 13 wt %; about 14 wt %; about 15 wt %; about 16 wt %; about 17 wt %; about 18 wt %; about 19 wt %; about 20 wt %; about 21 wt %; about 22 wt %; about 23 wt %; about 24 wt %; about 25 wt %, about 30%, about 33 wt %; 37 wt %; or about 40 wt %. In some embodiments, a therapeutic composition includes hydroxypropylcellulose in an amount of at least about 20 wt %.

In some embodiments, a therapeutic composition includes hydroxyproylcellulose in an amount of about 75 mg to about 125 mg; about 80 mg to about 120 mg; about 85 mg to about 115 mg; about 90 mg to about 110 mg; or about 95 mg to about 105 mg. In some embodiments, a therapeutic composition includes hydroxypropylcellulose in an amount of about 75 mg; about 80 mg; about 85 mg; about 90 mg; about 95 mg; about 100 mg; about 105 mg; about 110 mg; about 115 mg; about 120 mg; or about 125 mg.

In some embodiments, a therapeutic composition includes ethylcellulose. In some embodiments, suitable ethylcellulose includes an ethoxyl content of about 45% to about 47%. In some embodiments, suitable ethylcellulose includes an ethoxyl content of about 45%; about 46%; or about 47%.

An example of suitable commercially available ethylcellulose includes Ethocel Medium 70 by Dow Chemical.

In some embodiments, a therapeutic composition includes ethylcellulose in an amount of about 15 wt % to about 25 wt %; about 18 wt % to about 22 wt %; or about 19 wt % to about 21 wt %. In some embodiments, a therapeutic composition includes ethylcellulose in an amount of about 15 wt %; about 16 wt %; about 17 wt %; about 18 wt %; about 19 wt %; about 20 wt %; about 21 wt %; about 22 wt %; about 23 wt %; about 24 wt %; or about 25 wt %. In some embodiments, a therapeutic composition includes ethylcellulose in an amount of about 20.41 wt %.

In some embodiments, a therapeutic composition includes ethylcellulose in an amount of about 75 mg to about 400 mg; about 75 mg to about 375 mg; about 75 mg to about 350 mg; about 75 mg to about 325 mg; about 75 mg to about 300 mg; about 75 mg to about 275 mg; about 75 mg to about 250 mg; about 75 mg to about 225 mg; about 75 mg to about 200 mg; about 75 mg to about 175 mg; about 75 mg to about 150 mg; about 75 mg to about 125 mg; about 80 mg to about 120 mg; about 85 mg to about 115 mg; about 90 mg to about 110 mg; or about 95 mg to about 105 mg. In some embodiments, a therapeutic composition includes ethylcellulose in an amount of about 75 mg; about 80 mg; about 85 mg; about 90 mg; about 95 mg; about 100 mg; about 105 mg; about 110 mg; about 115 mg; about 120 mg; about 125 mg; about 150 mg; about 175 mg; about 200 mg; about 225 mg; about 250 mg; about 275 mg; about 300 mg; about 325 mg; about 350 mg; about 375 mg; or about 400 mg.

Following the teachings set forth herein, other suitable gel forming agents can include one or more of the following polymers: polyvinyl alcohol, hydroxypropyl methyl cellulose, carbomers, ethyl cellulose, cellulose acetate, cellulose acetate propionate, cellulose acetate butyrate, cellulose acetate phthalate and cellulose triacetate, cellulose ether, cellulose ester, cellulose ester ether, and cellulose, acrylic resins comprising copolymers synthesized from acrylic and methacrylic acid esters, the acrylic polymer may be selected from the group consisting of acrylic acid and methacrylic acid copolymers, methyl methacrylate copolymers, ethoxyetlryl methacrylates, cyanoetlryl methacrylate, poly(acrylic acid), poly(methacrylic acid), methacrylic acid alkylamide copolymer, poly(methyl methacrylate), polymethacrylate, poly(methyl methacrylate)copolymer, polyacrylamide, aminoalkyl methacrylate copolymer, poly(methacrylic acid anhydride), and glycidyl methacrylate copolymers.

Any of the above described polymers can be combined together or combined with other suitable polymers, and such combinations are within the scope of the present invention.

In one embodiment, the present invention can prevent less than or equal to about 95%, 94%, 70%, 60%, 54%, 50%, 45%, 40%, 36%, 32%, 30%, 27%, 20%, 10%, 9%, 6%, 5% or 2% of the total amount of a pharmaceutical susceptible to abuse in a dosage form from being recovered from a solvent. Alternatively, in some embodiments the present invention can prevent less than or equal to about 95%, 94%, 70%, 60%, 54%, 50%, 45%, 40%, 36%, 32%, 30%, 27%, 20%, 10%, 9%, 6%, 5% or 2% of the total amount of precursor compound from being chemically converted from precursor compound to a drug susceptible to abuse. Alternatively, in some embodiments the present invention can prevent less than or equal to about 95%, 94%, 70%, 60%, 54%, 50%, 45%, 40%, 36%, 32%, 30%, 27%, 20%, 10%, 9%, 6%, 5% or 2% of the total amount of any drug which is converted from being recovered.

The above described agents can be optimized in light of the teachings set forth herein as necessary or desired in terms of viscosity, molecular weight, etc. The present invention can be used to manufacture immediate release and controlled drug release formulations. Controlled release formulations can include delayed release, bi-modal and tri-modal release, extended and sustained release oral solid dosage preparations. In some embodiments, immediate release therapeutic compositions of the present invention include polymers associated with controlled release formulations. In some embodiments, immediate release therapeutic compositions of the present invention include polymers associated with controlled release formulations in an amount of at least about 75 wt %; at least about 70 wt %; at least about 65 wt %; at least about 60 wt %; at least about 55 wt %; at least about 50 wt %; at least about 45 wt %; at least about 40 wt %; at least about 35 wt %; at least about 30 wt %; at least about 25 wt %; at least about 20 wt %; at least about 15 wt %; at least about 10 wt %; or at least about 5 wt %.

Ratios of Constituents

In some embodiments, a first gelling polymer is present in combination with one or more different constituents (e.g. a gel forming polymer or a triglyceride).

In some embodiments, a first gelling polymer is present in combination with one or more different gel forming polymers. In certain embodiments, the first gel forming polymer is hydroxypropylcellulose and a second polymer is an ethylene oxide such as polyethylene oxide. In certain embodiments, the first gel forming polymer is ethylcellulose and a second polymer is an ethylene oxide such as polyethylene oxide. In certain embodiments, the first gel forming polymer is hydroxypropylcellulose and a second polymer is ethylcellulose.

In one embodiment, the ratio between a first gel forming polymer and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In some embodiments, two different gel forming polymers can be used. As used herein, "different" can be understood to mean chemically different and/or physically distinct, such as differences in viscosity, particle size, shape, density, etc. In some embodiments, a composition includes three or more gel forming polymers, wherein the ratio between any two gel forming polymers is in accord with the above ratios.

In one embodiment, the ratio between hydroxypropylcellulose and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between ethylcellulose and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between polyethylene oxide and another gel forming polymer on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In one embodiment, the ratio between hydroxypropylcellulose and polyethylene oxide on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between ethylcellulose and polyethylene oxide on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In one embodiment, the ratio between hydroxypropylcellulose and ethylcellulose on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In other embodiments, the ratio of hydroxypropylcellulose and another gel forming polymer on a weight basis is between or is between about 5:1 and 1:10. In other embodiments, the ratio of hydroxypropylcellulose and another gel forming polymer on a weight basis is between or is between about 4:1 and 1:10. In other embodiments, the ratio of hydroxypropylcellulose and another gel forming polymer on a weight basis is between or is between about 6:1 and 1:10. In other embodiments, the ratio of hydroxypropylcellulose and another gel forming polymer on a weight basis is between or is between about 7:1 and 1:10. In other embodiments, the ratio of hydroxypropylcellulose and another gel forming polymer on a weight basis is between or is between about 8:1 and 1:10. In other embodiments, the ratio of hydroxypropylcellulose and another gel forming polymer on a weight basis is between or is between about 9:1 and 1:10. In other embodiments, the ratio of hydroxypropylcellulose and another gel forming polymer on a weight basis is between or is between about 10:1 and 1:10.

In other embodiments, the ratio of polyethylene oxide and another gel forming polymer on a weight basis is between or is between about 5:1 and 1:10. In other embodiments, the ratio of polyethylene oxide and another gel forming polymer on a weight basis is between or is between about 4:1 and 1:10. In other embodiments, the ratio of polyethylene oxide and another gel forming polymer on a weight basis is between or is between about 6:1 and 1:10. In other embodiments, the ratio of polyethylene oxide and another gel forming polymer on a weight basis is between or is between about 7:1 and 1:10. In other embodiments, the ratio of polyethylene oxide and another gel forming polymer on a weight basis is between or is between about 8:1 and 1:10. In other embodiments, the ratio of polyethylene oxide and another gel forming polymer on a weight basis is between or is between about 9:1 and 1:10. In other embodiments, the ratio of polyethylene oxide and another gel forming polymer on a weight basis is between or is between about 10:1 and 1:10.

In other embodiments, the ratio of ethylcellulose and another gel forming polymer on a weight basis is between or is between about 5:1 and 1:10. In other embodiments, the ratio of ethylcellulose and another gel forming polymer on a weight basis is between or is between about 4:1 and 1:10. In other embodiments, the ratio of ethylcellulose and another gel forming polymer on a weight basis is between or is between about 6:1 and 1:10. In other embodiments, the ratio of ethylcellulose and another gel forming polymer on a weight basis is between or is between about 7:1 and 1:10. In other embodiments, the ratio of ethylcellulose and another gel forming polymer on a weight basis is between or is between about 8:1 and 1:10. In other embodiments, the ratio of ethylcellulose and another gel forming polymer on a weight basis is between or is between about 9:1 and 1:10. In other embodiments, the ratio of ethylcellulose and another gel forming polymer on a weight basis is between or is between about 10:1 and 1:10.

In certain embodiments, a gel forming polymer which forms a gel in a polar solvent is present in combination with a gel forming polymer which forms a gel in a non-polar solvent. In some embodiments, the ratio between a gel forming polymer which forms a gel in a polar solvent and a gel forming polymer which forms a gel in a non-polar solvent on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In other embodiments, the ratio of a gel forming polymer which forms a gel in a polar solvent and a gel forming polymer which forms a gel in a non-polar solvent on a weight basis is between about 5:1 and 1:10. In other embodiments, the ratio of a gel forming polymer which forms a gel in a polar solvent and a gel forming polymer which forms a gel in a non-polar solvent on a weight basis is between or is between about 4:1 and 1:10. In other embodiments, the ratio of a gel forming polymer which forms a gel in a polar solvent and a gel forming polymer which forms a gel in a non-polar solvent on a weight basis is between or is between about 6:1 and 1:10. In other embodiments, the ratio of a gel forming polymer which forms a gel in a polar solvent and a gel forming polymer which forms a gel in a non-polar solvent on a weight basis is between or is between about 7:1 and 1:10. In other embodiments, the ratio of a gel forming polymer which forms a gel in a polar solvent and a gel forming polymer which forms a gel in a non-polar solvent on a weight basis is between or is between about 8:1 and 1:10. In other embodiments, the ratio of a gel forming polymer which forms a gel in a polar solvent and a gel forming polymer which forms a gel in a non-polar solvent on a weight basis is between or is between about 9:1 and 1:10. In other embodiments, the ratio of a gel forming polymer which forms a gel in a polar solvent and a gel forming polymer which forms a gel in a non-polar solvent on a weight basis is between or is between about 10:1 and 1:10.

In some embodiments, a first gelling polymer is present in combination with one or more triglycerides. In some embodiments, the ratio between a first gelling polymer and a triglyceride on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In certain embodiments the first gelling polymer is hydroxypropylcellulose. In certain embodiments where the first gelling polymer is hydroxypropylcellulose, the triglyceride is tristearin. In one embodiment, the ratio between hydroxypropylcellulose and tristearin on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In certain embodiments where the first gelling polymer is hydroxypropylcellulose, the triglyceride is hydrogenated palm oil. In one embodiment, the ratio between hydroxypropylcellulose and hydrogenated palm oil on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In certain embodiments the first gelling polymer is polyethylene oxide. In certain embodiments where the first gelling polymer is polyethylene oxide, the triglyceride is tristearin. In one embodiment, the ratio between polyethylene oxide and tristearin on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10. In certain embodiments where the first gelling polymer is polyethylene oxide, the triglyceride is hydrogenated palm oil. In one embodiment, the ratio between polyethylene oxide and hydrogenated palm oil on a weight basis is or is about one of the following ratios: 10:1, 9:1, 7:1, 6:1, 5:1, 4:1, 3:1, 2:1, 1:1, 1:2, 1:3, 1:4, 1:5, 1:6, 1:7, 1:8, 1:9, and 1:10.

In other embodiments, the ratio of a first gelling polymer and a triglyceride on a weight basis is between or is between about 5:1 and 1:10. In other embodiments, the ratio of a first gelling polymer and a triglyceride on a weight basis is between or is between about 4:1 and 1:10. In other embodiments, the ratio of a first gelling polymer and a triglyceride on a weight basis is between or is between about 6:1 and 1:10. In other embodiments, the ratio of a first gelling polymer and a triglyceride on a weight basis is between or is between about 7:1 and 1:10. In other embodiments, the ratio of a first gelling polymer and a triglyceride on a weight basis is between or is between about 8:1 and 1:10. In other embodiments, the ratio of a first gelling polymer and a triglyceride on a weight basis is between or is between about 9:1 and 1:10. In other embodiments, the ratio of a first gelling polymer and a triglyceride on a weight basis is between or is between about 10:1 and 1:10.

In certain embodiments the first gelling polymer is hydroxypropylcellulose. In certain embodiments where the first gelling polymer is hydroxypropylcellulose, the triglyceride is tristearin. In some embodiments, the ratio of hydroxypropylcellulose and tristearin on a weight basis is between or is between about 5:1 and 1:10. In other embodiments, the ratio of the ratio of hydroxypropylcellulose and tristearin on a weight basis is between or is between about 4:1 and 1:10. In other embodiments, the ratio of the ratio of hydroxypropylcellulose and tristearin on a weight basis is between or is between about 6:1 and 1:10. In other embodiments, the ratio of the ratio of hydroxypropylcellulose and tristearin on a weight basis is between or is between about 7:1 and 1:10. In other embodiments, the ratio of the ratio of hydroxypropylcellulose and tristearin on a weight basis is between or is between about 8:1 and 1:10. In other embodiments, the ratio the ratio of hydroxypropylcellulose and tristearin on a weight basis is between or is between about 9:1 and 1:10. In other embodiments, the ratio of the ratio of hydroxypropylcellulose and tristearin on a weight basis is between or is between about 10:1 and 1:10.

In certain other embodiments where the first gelling polymer is hydroxypropylcellulose, the triglyceride is hydrogenated palm oil. In some embodiments, the ratio of hydroxypropylcellulose and hydrogenated palm oil on a weight basis is between or is between about 5:1 and 1:10. In other embodiments, the ratio of the ratio of hydroxypropylcellulose and hydrogenated palm oil on a weight basis is between or is between about 4:1 and 1:10. In other embodiments, the ratio of the ratio of hydroxypropylcellulose and hydrogenated palm oil on a weight basis is between or is between about 6:1 and 1:10. In other embodiments, the ratio of the ratio of hydroxypropylcellulose and hydrogenated palm oil on a weight basis is between or is between about 7:1 and 1:10. In other embodiments, the ratio of the ratio of hydroxypropylcellulose and hydrogenated palm oil on a weight basis is between or is between about 8:1 and 1:10. In other embodiments, the ratio the ratio of hydroxypropylcellulose and hydrogenated palm oil on a weight basis is between or is between about 9:1 and 1:10. In other embodiments, the ratio of the ratio of hydroxypropylcellulose and hydrogenated palm oil on a weight basis is between or is between about 10:1 and 1:10.

In certain embodiments the first gelling polymer is polyethylene oxide. In certain embodiments where the first gelling polymer is polyethylene oxide, the triglyceride is tristearin. In some embodiments, the ratio of polyethylene oxide and tristearin on a weight basis is between or is between about 5:1 and 1:10. In other embodiments, the ratio of the ratio of polyethylene oxide and tristearin on a weight basis is between or is between about 4:1 and 1:10. In other embodiments, the ratio of the ratio of polyethylene oxide and tristearin on a weight basis is between or is between about 6:1 and 1:10. In other embodiments, the ratio of the ratio of polyethylene oxide and tristearin on a weight basis is between or is between about 7:1 and 1:10. In other embodiments, the ratio of the ratio of polyethylene oxide and tristearin on a weight basis is between or is between about 8:1 and 1:10. In other embodiments, the ratio the ratio of polyethylene oxide and tristearin on a weight basis is between or is between about 9:1 and 1:10. In other embodiments, the ratio of the ratio of polyethylene oxide and tristearin on a weight basis is between or is between about 10:1 and 1:10.

In certain other embodiments where the first gelling polymer is polyethylene oxide, the triglyceride is hydrogenated palm oil. In some embodiments, the ratio of polyethylene oxide and hydrogenated palm oil on a weight basis is between or is between about 5:1 and 1:10. In other embodiments, the ratio of the ratio of polyethylene oxide and hydrogenated palm oil on a weight basis is between or is between about 4:1 and 1:10. In other embodiments, the ratio of the ratio of polyethylene oxide and hydrogenated palm oil on a weight basis is between or is between about 6:1 and 1:10. In other embodiments, the ratio of the ratio of polyethylene oxide and hydrogenated palm oil on a weight basis is between or is between about 7:1 and 1:10. In other embodiments, the ratio of the ratio of polyethylene oxide and hydrogenated palm oil on a weight basis is between or is between about 8:1 and 1:10. In other embodiments, the ratio the ratio of polyethylene oxide and hydrogenated palm oil on a weight basis is between or is between about 9:1 and 1:10. In other embodiments, the ratio of the ratio of polyethylene oxide and hydrogenated palm oil on a weight basis is between or is between about 10:1 and 1:10.

4. Additional Constituents

The present invention can also optionally include other ingredients to enhance dosage form manufacture from a pharmaceutical composition of the present invention and/or alter the release profile of a dosage forming including a pharmaceutical composition of the present invention, including fillers, disintegrants, glidants, and lubricants.

a. Fillers

Some embodiments of the present invention include one or more pharmaceutically acceptable fillers/diluents. In some embodiments, a therapeutic composition includes any suitable binder or filler. In some embodiments, a therapeutic composition includes microcrystalline cellulose. In some embodiments, suitable microcrystalline cellulose can have an average particle size ranging from 20 to about 200 µm, preferably about 100 µm. In some embodiments, the density ranges from 1.512-1.668 g/cm$^3$. In certain embodiments, suitable microcrystalline cellulose should have molecular weight of about 36,000. Other ingredients can include sugars and/or polyols.

An example of suitable commercially available microcrystalline cellulose includes Avicel PH102 by FMC Corporation.

In some embodiments, a therapeutic composition includes microcrystalline cellulose in an amount of about 20 wt % to about 35 wt %; about 22 wt % to about 32 wt %; about 24 wt % to about 30 wt %; or about 26 wt % to about 28 wt %.

In some embodiments, a therapeutic composition includes microcrystalline cellulose in an amount of about 20 wt %; about 21 wt %; about 22 wt %; about 23 wt %; about 24 wt %; about 25 wt %; about 26 wt %; about 27 wt %; about 28 wt %; about 29 wt %; about 30 wt %; about 31 wt %; about 32 wt %; about 33 wt %; about 34 wt %; or about 35 wt %. In some embodiments, a therapeutic composition includes about 26.94 wt %.

In certain embodiments, a therapeutic composition includes microcrystalline cellulose in an amount of about 100 mg to about 160 mg; about 105 mg to about 155 mg; about 110 mg to about 150 mg; about 115 mg to about 145 mg; about 120 mg to about 140 mg; about 125 mg to about 135 mg; or about 120 mg to about 135 mg. In certain embodiments, a therapeutic composition includes microcrystalline cellulose in an amount of about 100 mg; about 105 mg; about 110 mg; about 115 mg; about 120 mg; about 125 mg; about 130 mg; about 135 mg; about 140 mg; about 145 mg; about 150 mg; or 155 mg. In some embodiments, a therapeutic composition includes about 132 mg microcrystalline cellulose.

In some embodiments of the invention, the fillers which can be present at about 10 to 65 percent by weight on a dry weight basis, also function as binders in that they not only impart cohesive properties to the material within the formulation, but can also increase the bulk weight of a directly compressible formulation (as described below) to achieve an acceptable formulation weight for direct compression. In some embodiments, additional fillers need not provide the same level of cohesive properties as the binders selected, but can be capable of contributing to formulation homogeneity and resist segregation from the formulation once blended. Further, preferred fillers do not have a detrimental effect on the flowability of the composition or dissolution profile of the formed tablets.

b. Disintegrants

In some embodiments, the present invention can include one or more pharmaceutically acceptable disintegrants. Such disintegrants are known to a skilled artisan. In some embodiments, a therapeutic composition includes crospovidone (such as Polyplasdone® XL) having a particle size of about 400 microns and a density of about 1.22 g/ml. In some embodiments, disintegrants can include, but are not limited to, sodium starch glycolate (Explotab®) having a particle size of about 104 microns and a density of about 0.756 g/ml, starch (e.g., Starch 21) having a particle size of about 2 to about 32 microns and a density of about 0.462 g/ml, and croscarmellose sodium (Ac-Di-Sol) having a particle size of about 37 to about 73.7 microns and a density of about 0.529 g/ml. The disintegrant selected should contribute to the compressibility, flowability and homogeneity of the formulation. Further the disintegrant can minimize segregation and provide an immediate release profile to the formulation. An immediate release drug product is understood in the art to allow drugs to dissolve with no intention of delaying or prolonging dissolution or absorption of the drug upon administration, as opposed to products which are formulated to make the drug available over an extended period after administration. In some embodiments, the disintegrant(s) are present in an amount from about 2 wt % to about 25 wt %.

In some embodiments, a therapeutic composition includes crospovidone in an amount of about 15 wt % to about 25 wt %; about 18 wt % to about 22 wt %; or about 19 wt % to about 21 wt %. In some embodiments, a therapeutic composition includes crospovidone in an amount of about 15 wt %; about 16 wt %; about 17 wt %; about 18 wt %; about 19 wt %; about 20 wt %; about 21 wt %; about 22 wt %; about 23 wt %; about 24 wt %; or about 25 wt %. In some embodiments, a therapeutic composition includes crospovidone in an amount of about 20.41 wt %.

In some embodiments, a therapeutic composition includes crospovidone in an amount of about 75 mg to about 125 mg; about 80 mg to about 120 mg; about 85 mg to about 115 mg; about 90 mg to about 110 mg; or about 95 mg to about 105 mg. In some embodiments, a therapeutic composition includes crospovidone in an amount of about 75 mg; about 80 mg; about 85 mg; about 90 mg; about 95 mg; about 100 mg; about 105 mg; about 110 mg; about 115 mg; about 120 mg; or about 125 mg.

c. Glidants

In one embodiment, the present invention can include one or more pharmaceutically acceptable glidants, including but not limited to colloidal silicon dioxide. In one embodiment, colloidal silicon dioxide (Cab-O-Sil®) having a density of about 0.029 to about 0.040 g/ml can be used to improve the flow characteristics of the formulation. Such glidants can be provided in an amount of from about 0.1 wt % to about 1 wt %; about 0.2 wt % to about 0.8 wt %, or about 0.2 to about 6 wt %. In some embodiments, a therapeutic composition includes a glidant in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %. In some embodiments, a therapeutic composition includes a glidant in an amount of about 0.41 wt %. In some embodiments, a therapeutic composition includes a glidant in an amount of about 1 mg to about 10 mg; about 1 mg to about 5 mg; or about 1 mg to about 3 mg. In some embodiments, a therapeutic composition includes a glidant in an amount of about 1 mg; about 2 mg; about 3 mg; about 4 mg; about 5 mg; about 6 mg; about 7 mg; about 8 mg; about 9 mg; or about 10 mg.

It will be understood, based on this invention, however, that while colloidal silicon dioxide is one particular glidant, other glidants having similar properties which are known or to be developed could be used provided they are compatible with other excipients and the active ingredient in the formulation and which do not significantly affect the flowability, homogeneity and compressibility of the formulation.

d. Lubricants

In one embodiment, the present invention can include one or more pharmaceutically acceptable lubricants, including but not limited to magnesium stearate. In some embodiments, magnesium stearate has a particle size of about 450 to about 550 microns and a density of about 1.00 to about 1.80 g/ml. In some embodiments of the present invention, a therapeutic composition includes magnesium stearate having a particle size of from about 5 to about 50 microns and a density of from about 0.1 to about 1.1 g/ml. In certain embodiments, magnesium stearate can contribute to reducing friction between a die wall and a pharmaceutical composition of the present invention during compression and can ease the ejection of the tablets, thereby facilitating processing. In some embodiments, the lubricant resists adhesion to punches and dies and/or aid in the flow of the powder in a hopper and/or into a die. In some embodiments, suitable lubricants are stable and do not polymerize within the formulation once combined. Other lubricants which exhibit acceptable or comparable properties include stearic acid, hydrogenated oils, sodium stearyl fumarate, polyethylene glycols, and Lubritab®.

In certain embodiments, a therapeutic composition includes lubricant in an amount of about 0.1 wt % to about 5 wt %; about 0.1 wt % to about 3 wt %; about 0.1 wt % to about 1 wt %; or about 0.1 wt % to about 0.5 wt %. In some embodiments, a therapeutic composition includes lubricant in an amount of about 0.1 wt %; about 0.2 wt %; about 0.3 wt %; about 0.4 wt %; about 0.5 wt %; about 0.6 wt %; about 0.7 wt %; about 0.8 wt %; about 0.9 wt %; or about 1 wt %. In some embodiments, a therapeutic composition includes lubricant in an amount of about 0.5 mg to about 5 mg; about 0.5 mg to about 3 mg; or 0.5 mg to about 1.5 mg. In some embodiments, a therapeutic composition includes lubricant in an amount of about 0.5 mg; about 1 mg; about 1.5 mg; about 2 mg; about 2.5 mg; about 3 mg; about 4 mg; about 5 mg; about 6 mg; about 7 mg; about 8 mg; about 9 mg; or about 10 mg.

In certain embodiments, the most important criteria for selection of the excipients are that the excipients should achieve good content uniformity and release the active ingredient as desired. The excipients, by having excellent binding properties, and homogeneity, as well as good compressibility, cohesiveness and flowability in blended form, minimize segregation of powders in the hopper during direct compression.

B. Methods of Making

In some embodiments, any of the constituents may or may not be sequestered from the other constituents during the manufacturing or in the final dosage form (e.g., tablet or capsule). In some embodiments, one or more of the constituents (e.g., gel forming polymers, including polyethylene oxide, hydroxypropylcellulose, and ethylcellulose, triglycerides, including tristearin and hydrogenated palm kernel oil, disintegrant, fillers and/or drug susceptible to abuse) may be sequestered. In some embodiments, one or more of the constituents (e.g., gel forming polymers, including polyethylene oxide, hydroxypropylcellulose, and ethylcellulose, triglycerides, including tristearin and hydrogenated palm kernel oil, disintegrant, fillers and/or drug susceptible to abuse) is blended and/or admixed such that all or a portion of the constituents are in contact with other constituents and/or are not sequestered.

A pharmaceutical composition of the present invention including one or more drugs, one or more triglycerides, and optionally other ingredients, can be suitably modified and processed to form a dosage form of the present invention. In this manner, an abuse deterrent composition comprising triglycerides, gel forming agents, emetics, and any other optional ingredients can be layered onto, coated onto, applied to, admixed with, formed into a matrix with, and/or blended with a drug and optionally other ingredients, thereby providing a therapeutic composition of the present invention.

Suitable formulations and dosage forms of the present invention include but are not limited to powders, caplets, pills, suppositories, gels, soft gelatin capsules, capsules and compressed tablets manufactured from a pharmaceutical composition of the present invention. The dosage forms can be any shape, including regular or irregular shape depending upon the needs of the artisan.

Compressed tablets including the pharmaceutical compositions of the present invention can be direct compression tablets or non-direct compression tablets. In some embodiments, a dosage form of the present invention can be made by wet granulation, and dry granulation (e.g., slugging or roller compaction). The method of preparation and type of excipients are selected to give the tablet formulation desired physical characteristics that allow for the rapid compression of the tablets. After compression, the tablets must have a number of additional attributes such as appearance, hardness, disintegrating ability, and an acceptable dissolution profile.

Choice of fillers and other excipients typically depend on the chemical and physical properties of the drug, behavior of the mixture during processing, and the properties of the final tablets. Adjustment of such parameters is understood to be within the general understanding of one skilled in the relevant art. Suitable fillers and excipients are described in more detail above.

The manufacture of a dosage form of the present invention can involve direct compression and wet and dry granulation methods, including slugging and roller compaction. In some embodiments, it is preferred to use direct compression techniques because of the lower processing time and cost advantages.

Accordingly, and as described further below, a directly compressible pharmaceutical composition of the present invention can be designed following the teachings set forth herein that can deter one or more of a) parenteral abuse of a drug, b) inhalation abuse of a drug, c) oral abuse of a drug, and d) conversion of a drug using illicit processes.

Steps for making the compositions or dosage forms include the step of providing one or more drugs described above and a triglyceride having a desired melting point and solubility in non-polar solvent as described above and/or providing an amount of gel forming polymer having a desired molecular weight or viscosity as described above, a disintegrant, and/or other ingredients in the amounts as described above.

By controlling the melting point and/or solubility of the triglyceride, a therapeutic composition suitable for use to deter drug abuse can be formed. In some embodiments, in addition to the routes of abuse noted above, a composition according to the present invention inhibits the crystallization and extraction of a drug susceptible to abuse from a drug or precursor compound.

C. Abuse Deterrence

1. Interference with Crystallization and Extraction of A Drug Susceptible to Abuse Compositions of some embodiments of the present invention may restrict, reduce or diminish the crystallization and extractability of a drug susceptible to abuse that is converted by illicit means from a precursor drug, such as methamphetamine or methionine converted from a precursor pseudoephedrine, obtained from pseudoephedrine dosage forms. Without being bound by a particular mode of action, in some embodiments, therapeutic compositions of the present invention can interfere with the crystallization of a drug susceptible to abuse by forming a complex in solution with the converted drug. The triglyceride present in compositions of some embodiments of the present invention is soluble in non-polar organic solvents. Examples of such solvents include, but are not limited to, cyclohexane, nonane, octane, heptane, pentane, and mixtures thereof, including, but not limited to Coleman Fuel (also referred to as naptha or white gas).

Conversion of certain precursor compounds, including pseudoephedrine, to methamphetamine may be attempted by a number of methods, including the Nazi Method, the Red Phosphorous Method, and the Shake and Bake Method. In some embodiments, therapeutic compositions of the present invention inhibit extraction of a converted drug from solution, such as the "one-pot" solution of the Shake and Bake Method.

Tristearin

In one embodiment, a therapeutic composition includes pseudoephedrine HCl, polyethylene oxide, hydroxypropylcellulose, microcrystalline cellulose, tristearin, crospovidone, and magnesium stearate. The therapeutic composition may include pseudoephedrine HCl in an amount of about 6.1 wt %, hydroxypropylcellulose in an amount of about 20.4 wt %; microcrystalline cellulose in an amount of about 39.4 wt %, tristearin in an amount of about 10.2 wt % to crospovidone in an amount of about 20.4 wt %; and magnesium stearate in an amount of about 0.4 wt %. A 490 mg tablet of such formulation may include 30 mg pseudoephedrine HCl; 15 mg polyethylene oxide; 100 mg hydroxypropylcellulose; 193 mg microcrystalline cellulose; 50 mg tristearin; 100 mg crospovidone; and 2 mg magnesium stearate. In such embodiment, suitable hydroxypropylcellulose has a molecular weight of about 1,150,000 and a viscosity of about 1,500 to about 3,000. Such therapeutic composition may provide an immediate release product.

One embodiment of the present invention is as follows:

Formulation 1

| Component | mg per Tablet | % (wt/wt) |
|---|---|---|
| Pseudoephedrine HCl | 30 | 6.1 |
| Polyox WSR polethylene oxide | 15 | 3.1 |
| Klucel HF hydroxypropylcellulose | 100 | 20.4 |
| Avicel PH102 microcrystalline cellulose | 193 | 39.4 |
| Dynasan 118 tristearin | 50 | 10.2 |
| Polyplasdone XL crospovidone | 100 | 20.4 |
| Magnesium Stearate | 2 | 0.4 |
| Total | 490 | 100.0 |

The formulation demonstrates an immediate release product which can inhibit the extraction of methamphetamine or methcathinone from a non-polar solvent by forming a complex with the methamphetamine or methcathinone in solution. Examples of such solvents include, but are not limited to Coleman Fuel.

The Shake and Bake Method is generally known to be employed in small scale (gram quantities) production of methamphetamine. Formulation 1 was tested for interference with extraction of converted methamphetamine.

100 pseudoephedrine tablets of Formulation 1 were ground with a coffee grinder. The powdered pills were then mixed with ½ cups (or about 180 mL) of ammonium nitrate. The powder was transferred to a 1 L bottle and combined with 450 mL COLEMAN® fuel, ½ bottle cap of crushed sodium hydroxide (gram quantity was recorded), and 1 bottle cap of water (mL quantity was recorded). The bottle was closed and the mixture stirred with a magnetic stir bar for 5 minutes before the pressure was released. ½ caps of crushed sodium hydroxide (gram quantity was recorded) were added every 20 minutes while stirring, until a total of 30 g of sodium hydroxide was added over 2 hours. Next, the mixture was filtered through fluted filter paper into a 1 L flask. Hydrogen chloride gas was bubbled through the filtrate for approximately 1 minute. The precipitate was collected by decanting off the liquid or filtration for about 30 minutes. The resulting precipitate was a sticky semi-solid and comprised about 50% methamphetamine HCl.

Upon analyzing the dried solid, it was found that overall reaction yield of methamphetamine HCl recovered was 5.7%. The typical yield of methamphetamine HCl from a commercially available product, such as SUDAFED®, is greater than about 80%.

Hydrogenated Palm Kernel Oil

In one embodiment, a therapeutic composition includes pseudoephedrine HCl, polyethylene oxide, hydroxypropylcellulose, microcrystalline cellulose, hydrogenated palm kernel oil, crospovidone, and magnesium stearate. The therapeutic composition may include pseudoephedrine HCl in an amount of about 6.1 wt %, hydroxypropylcellulose in an amount of about 20.4 wt %; microcrystalline cellulose in an amount of about 39.4 wt %, hydrogenated palm kernel oil in an amount of about 10.2 wt % crospovidone in an amount of about 20.4 wt %; and magnesium stearate in an amount of about 0.4 wt %. A 490 mg tablet of such formulation may include 30 mg pseudoephedrine HCl; 15 mg polyethylene oxide; 100 mg hydroxypropylcellulose; 193 mg microcrystalline cellulose; 50 mg hydrogenated palm kernel oil; 100 mg crospovidone; and 2 mg magnesium stearate. In such embodiment, suitable hydroxypropylcellulose has a molecular weight of about 1,150,000 and a viscosity of about 1,500 to about 3,000. Such therapeutic composition may provide an immediate release product.

One embodiment of the present invention is as follows:

Formulation 2

| Component | mg per Tablet | % (wt/wt) |
|---|---|---|
| Pseudoephedrine HCl | 30 | 6.1 |
| Polyox WSR polethylene oxide | 15 | 3.1 |
| Klucel HF hydroxypropylcellulose | 100 | 20.4 |
| Avicel PH102 microcrystalline cellulose | 193 | 39.4 |
| Softisan 154 hydrogenated palm kernel oil | 50 | 10.2 |
| Polyplasdone XL crospovidone | 100 | 20.4 |
| Magnesium Stearate | 2 | 0.4 |
| Total | 490 | 100.00 |

The Shake and Bake Method is generally known to be employed in small scale (gram quantities) production of methamphetamine. Formulation 2 was tested for interference with extraction of converted methamphetamine.

100 pseudoephedrine tablets of Formulation 2 were ground with a coffee grinder. The powdered pills were then mixed with 4 cups (or about 180 mL) of ammonium nitrate. The powder was transferred to a 1 L bottle and combined with 450 mL COLEMAN® fuel, ½ bottle cap of crushed sodium hydroxide (gram quantity was recorded), and 1 bottle cap of water (mL quantity was recorded). The bottle was closed and the mixture stirred with a magnetic stir bar for 5 minutes before the pressure was released. ½ caps of crushed sodium hydroxide (gram quantity was recorded) were added every 20 minutes while stirring, until a total of 30 g of sodium hydroxide was added over 2 hours. Next, the mixture was filtered through fluted filter paper into a 1 L flask. Hydrogen chloride gas was bubbled through the filtrate for approximately 1 minute. The precipitate was collected by decanting off the liquid or filtration for about 30 minutes. The resulting precipitate was a sticky semi-solid and comprised about 50% methamphetamine HCl.

The typical yield from commercial product is greater than about 80%. Upon analyzing the dried solid, it was found that overall reaction yield of methamphetamine HCl recovered was 5.7%.

As used herein, the term "about" is understood to mean ±10% of the value referenced. For example, "about 45%" is understood to literally mean 40.5% to 49.5%.

A number of references have been cited, the entire disclosures of which are incorporated herein by reference.

I claim:

1. A therapeutic composition comprising:
   a pharmaceutically effective amount of pseudoephedrine or a salt thereof;
   a triglyceride in an amount of about 1 wt % to about 50 wt % of the therapeutic composition;
   hydroxypropylcellulose;
   polyethylene oxide; and
   a disintegrant selected from the group consisting of crospovidone, sodium starch glycolate and croscarmellose sodium;
   wherein the composition is a controlled release composition.

2. The therapeutic composition of claim 1, wherein the hydroxypropylcellulose has a viscosity of about 1,500 mPa to about 3,000 mPa at a concentration of 1% in water.

3. The therapeutic composition of claim 1, wherein the hydroxypropylcellulose has a molecular weight of about 1,150,000.

4. The therapeutic composition of claim 1, wherein the polyethylene oxide is present in an amount of about 3 wt % to about 7 wt %.

5. The therapeutic composition of claim 1, wherein the polyethylene oxide is present in an amount of about 5 wt % to about 10 wt %.

6. The therapeutic composition of claim 1, wherein the triglyceride has a melting point of about 50° C. to about 80° C.

7. The therapeutic composition of claim 1, wherein the triglyceride is tristearin.

8. The therapeutic composition of claim 1, wherein the disintegrant is crospovidone and is present in an amount of about 15 wt % to about 25 wt %.

9. The therapeutic composition of claim 1, wherein the disintegrant is crospovidone and is present in an amount of about 18 wt % to about 22 wt %.

10. The therapeutic composition of claim 1, further comprising a glidant.

11. The therapeutic composition of claim 10, wherein the glidant comprises colloidal silicon dioxide.

12. The therapeutic composition of claim 1, further comprising a lubricant.

13. The therapeutic composition of claim 12, wherein the lubricant comprises magnesium stearate.

14. The therapeutic composition of claim 1, wherein the composition is a suppository, capsule, caplet, pill, gel, soft gelatin capsule, or compressed tablet form.

15. The therapeutic composition of claim 1, wherein the composition is in unit dose form.

16. A composition suitable for reducing the chemical conversion of a precursor compound included in the composition to a drug susceptible to abuse comprising:
   a precursor compound that can be used in a chemical synthesis of a drug that is susceptible to abuse;
   a triglyceride in an amount of about 1 wt % to about 50 wt % of the therapeutic composition;
   hydroxypropylcellulose;
   polyethylene oxide; and
   a disintegrant selected from the group consisting of crospovidone, sodium starch glycolate and croscarmellose sodium;
   wherein the composition is a controlled release composition.

17. The composition of claim 16, wherein the precursor compound comprises pseudoephedrine.

18. The therapeutic composition of composition of claim 15, wherein the unit dose form is a direct compressed unit dose form.

19. A method of making a composition suitable for reducing the chemical conversion of precursor compound included in the composition to a drug susceptible to abuse comprising:
   providing ingredients comprising: a precursor compound that can be used in a chemical synthesis of a drug that is susceptible to abuse; a triglyceride in an amount of about 1 wt % to about 50 wt % of the therapeutic composition, hydroxypropylcellulose; polyethylene oxide, and a disintegrant selected from the group consisting of crospovidone, sodium starch glycolate, and croscarmellose sodium; and
   directly compressing the ingredients into a unit dose form;
   wherein the composition is a controlled release composition.

20. The therapeutic composition of claim 1, wherein the controlled release composition comprises a delayed release, a bi-modal release, a tri-modal release, an extended release, or a sustained release composition.

21. The therapeutic composition of claim 1, wherein the hydroxypropylcellulose is present in an amount of about 15 wt % to about 35 wt %.

22. The composition of claim 16, wherein the controlled release composition is a delayed release, a bi-modal release, a tri-modal release, an extended release, or a sustained release composition.

23. The composition of claim 16, wherein the hydroxypropylcellulose is present in an amount of about 15 wt % to about 35 wt %.

24. The method of claim 19, wherein the controlled release composition is a delayed release, a bi-modal release, a tri-modal release, an extended release, or a sustained release composition.

25. The method of claim 19, wherein the hydroxypropylcellulose is provided in an amount of about 15 wt % to about 35 wt %.

* * * * *

UNITED STATES PATENT AND TRADEMARK OFFICE
CERTIFICATE OF CORRECTION

| | | |
|---|---|---|
| PATENT NO. | : 11,723,885 B2 | |
| APPLICATION NO. | : 17/521581 | |
| DATED | : August 15, 2023 | |
| INVENTOR(S) | : Leech | |

It is certified that error appears in the above-identified patent and that said Letters Patent is hereby corrected as shown below:

In the Specification

<u>At Column 23</u>
Line 50, please change "0/0 cups" to -- ¾ cups --.

Signed and Sealed this
Twenty-ninth Day of October, 2024

Katherine Kelly Vidal
*Director of the United States Patent and Trademark Office*